(12) United States Patent
Hnasko et al.

(10) Patent No.: US 9,868,940 B2
(45) Date of Patent: Jan. 16, 2018

(54) BIOASSAY FOR CELL CONDITIONED MEDIA

(71) Applicant: The United States of America, as Represented by the Secretary of Agriculture, Washington, DC (US)

(72) Inventors: Robert M. Hnasko, Pinole, CA (US); Larry H. Stanker, Livermore, CA (US); Jeffery A. McGarvey, San Francisco, CA (US); Alice V. Lin, Livermore, CA (US)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 314 days.

(21) Appl. No.: 14/854,731

(22) Filed: Sep. 15, 2015

(65) Prior Publication Data

US 2016/0076002 A1    Mar. 17, 2016

Related U.S. Application Data

(60) Provisional application No. 62/050,446, filed on Sep. 15, 2014.

(51) Int. Cl.
*C12N 5/16*     (2006.01)
*G01N 33/50*    (2006.01)

(52) U.S. Cl.
CPC ......... *C12N 5/163* (2013.01); *G01N 33/5005* (2013.01)

(58) Field of Classification Search
None
See application file for complete search history.

*Primary Examiner* — Ram R Shukla
*Assistant Examiner* — Ellen J Marcsisin
(74) *Attorney, Agent, or Firm* — John D. Fado; Mark D. McNemar (57) ABSTRACT

Herein is described a novel hybridoma cell line (RMH359) and its use as a cellular bioassay to determine the efficacy of cell conditioned media (CCM) as a supplement used to support cell survival and promote growth in culture. This bioassay is the first to provide a measure of CCM bioactivity in support of hybridoma cells used in the generation and production of monoclonal antibodies.

2 Claims, 5 Drawing Sheets

BIOASSAY FOR CELL CONDITIONED MEDIA

FIELD OF THE INVENTION

The present invention relates to the generation of a novel cell line and its use as a cell-based bioassay to define the bioactivity of cell conditioned media to promote survival and growth of cultured cells.

BACKGROUND OF THE INVENTION

Cell conditioned media (CCM) such as macrophage conditioned medium (MCM) is an essential supplement necessary to support the survival and growth of hybridoma cells used in the production of monoclonal antibodies. The use of macrophage cell lines as part of hybridoma technology has proven to be an effective and inexpensive production source of macrophage derived growth factors. Despite the widespread use of MCM as a hybridoma culture supplement there is limited guidance and standardization for MCM production to achieve optimal hybridoma survival and growth. As an undefined supplement, significant variations in production of MCM may negatively impacts hybridoma cell survival and growth.

Monoclonal antibodies (mAbs) remain an essential molecular tool for the selective and specific detection of biological and chemical antigens. A defining property of a mAb is its recognition and binding to a single epitope, a characteristic that has been exploited to achieve exquisite antigen selectivity and discrimination. Hybridoma technology has allowed for the production of mAbs to specific antigens following splenocyte cell fusion from an immunized animal with immortalized myeloma-derived cell lines. The resulting hybridoma cells can be screened for selective mAb production and single cells cloned to yield an immortal hybridoma cell line for continuous production of a desired mAb.

Hybridoma technology has evolved along with modern cell culture practices, benefiting from refined cell media formulations and growth supplements, resulting in improved work flow and consistent mAb production. However, there remains a need for cost effective animal derived culture supplements to support hybridoma cell survival and growth. Indeed, newly formed hybrid cells require the addition of a cell feeder layer (i.e. macrophages) or supplementation with a cell-free conditioned medium for initial stabilization and growth (2, 3). The use of a feeder cell layer (4-6) imposes several disadvantages that include the interference with hybridoma cell growth and the introduction of potential contamination. Therefore, cell-free conditioned medium from continuous cell lines such as fibroblasts (7) or macrophages (8-10) has been commonly used as a culture medium supplement. Conditioned medium collected from the widely available macrophage J774A.1 cell line has been shown to improve hybridoma survival and cloning efficiency after cell fusion (8).

Efforts have been made to identify defined medium conditions to support hybridoma growth and increase the efficiency of antibody production. Proteins such as IL-1, tumor necrosis factor (TNF) (11), granulocyte-macrophage colony-stimulation factor (GM-CSF) (12), and IL-6 (13) have been shown to support hybridoma growth resulting in proprietary blends of define hybridoma growth medium. Although these commercial products can be effective they can be cost prohibitive and many laboratories rely on in-house production of MCM to support hybridoma growth during cell selection and cloning.

Limited guidance and standardization of MCM quality has been reported. This reflects the lack of a defined assay to evaluate the quality of MCM prior to use as a culture supplement. Herein is described optimization of conditioned media production designed to optimize MCM production by exploiting a new hybridoma cell line RMH359 that is dependent on J774A.1 derived MCM for survival and growth. Using RMH359 cells we define a novel cellular bioassay for the evaluation of MCM bioactivity in support of hybridoma cell survival and growth. Using the RMH359 bioassay we define optimal conditions for MCM production to achieve maximal bioactivity in support of hybridoma cells and provide a novel method for MCM validation and standardization that ensure hybridoma supplementation with high quality MCM.

The lack of an available method for standardization of MCM bioactivity has limited validation, optimization, and commercial production. Consequently, variations in batch production of MCM may result in low quality MCM that limits hybridoma viability and negatively impacts monoclonal antibody production. Herein is described a novel bioassay using a newly generated MCM-dependent RMH359 hybridoma cell line that can be used to validate MCM bioactivity and standardize production.

SUMMARY OF THE INVENTION

A hybridoma cell line having the identifying characteristics of ATCC deposit accession number PTA-122116 that requires MCM for survival and growth in culture.

A method for evaluating MCM hybridoma bioactivity using a MCM-dependent hybridoma cell line having the identifying characteristics of ATCC deposit accession number PTA-122116.

A method for defining optimal conditions for production of MCM using a MCM-dependent hybridoma cell line having the identifying characteristics of ATCC deposit accession number PTA-122116.

A method for defining an enhanced MCM that utilizes IL6 supplementation.

A method for the validation and standardization of MCM bioactivity or any CCM that is used to promote the growth, survival and function of cells in culture.

BRIEF DESCRIPTION OF THE DRAWINGS

FIG. 2A shows viability of RMH359 cells by MTT assay cultured 4 d in growth media supplemented with either 25% or 50% MCM obtained after 24 h of macrophage growth at seeding densities of either $1 \times 10^6$ or $6 \times 10^6$ cells. Data is expressed as % of no MCM supplement control. FIG. 2B shows dose-dependent increase in RMH359 hybridoma cells viability with MCM supplementation. The dose response of MCM primed with $1 \times 10^6$ macrophage cells for 24 h (●) or 72 h (○) is compared. Data from MTT assay is expressed as mean absorbance (AU; 570 nm)±SEM. The values obtained with no MCM (0%) are equivalent to assay background with no cells.

FIG. 3A RMH359 cell viability (grey bars) after 4 d growth supplemented with 50% MCM collected after 24, 48, and 72 h priming an initial density of $1\times10^6$ macrophage cells. Data is expressed as % of a no MCM control. The macrophage cell number was determined by counting (striped bars) at the time of MCM harvest. FIG. 3B. Stability of individual culture medium components after pre-incubation at 37° C. in 5% CO2 for 7 and 14 d on RMH359 cell viability. Fresh medium was prepared from stocks stored 14 d at 4° C. Complete medium is composed of advanced RPMI, 10% heat inactivated fetal bovine serum (PBS) and 40% macrophage conditioned media (MCM). PBS or MCM were individually pre-incubated 7 or 14 d at 37° C. in 5% CO2 before mixing with fresh media components. MTT assay was used to assess RMH359 cell viability after 4 d and data expressed as mean absorbance (AU; 570 nm)±SEM.

FIG. 4A Time-dependent Caspase 3/7 activity was determined in RMH359 cells (24, 48 and 72 h) supplemented with 50% MCM (●) or following MCM withdrawal (▼). Luminescent data from Caspase-Glo 3/7 assay is expressed as mean relative light units (RLU)±SEM. FIG. 4B In parallel cultures time-dependent RMH359 cell viability was determined using a CytoTox-Glo™ cytotoxicity assay in cultures supplemented with 50% MCM (●) or following MCM withdrawal (▼). Data is expressed as a mean relative fluorescence units (RFU)±SEM.

FIG. 5A RMH359 cells require MCM for survival and their growth is MCM dose-dependent. First order linear regression analysis of MCM supplementation of RMH359 cells (0-25%) results in correlation coefficients $r^2>0.98$. The efficacy of 24 h primed MCM (●) differs from 72 h primed MCM (▼) on RMH359 cell growth rates with slopes b[1] values of 0.025 and 0.014, respectively. FIG. 5B Dilutions of >40% MCM is non-linear and is best described by third order linear regression analysis resulting in correlation coefficients $r^2>0.999$. MTT assay was used to assess RMH359 cell viability and data expressed as mean absorbance±SEM.

STATEMENT OF DEPOSIT

The hybridoma RMH359 was deposited Apr. 23, 2015 under terms of the Budapest Treaty with the American Tissue Culture Collection (ATCC) P.O. Box 1549, Manassas, Va., 20108, USA under ATCC Accession No. PTA 122116. The microorganism deposit was made under the provisions of the "Budapest Treaty on the International Recognition of the Deposit of Microorganisms for the Purposes of Patent Procedure". All restrictions on the availability to the public of these deposited microorganisms will be irrevocably removed upon issuance of a United States patent based on this application. For the purposes of this invention, any hybridoma having the identifying characteristics of PTA-122116 including subcultures and variants thereof which have the identifying characteristics and activity as described herein are included.

DETAILED DESCRIPTION OF THE INVENTION

The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurement.

Any reference to RMH359 herein is synonymous with ATCC Accession no. PTA 122116, referenced in the deposit statement above.

Cell conditioned media (CCM) refers the liquid harvested from the culture of any primary cells or cell line in a liquid medium over a period of time that contains the biological products of those cells released into the culture medium.

Cell condition media (CCM) can be produced by growing any primary cell/s or cell line in culture over a period of time and harvesting the liquid medium. In general each cell type will release a distinct complement of biological factors into the liquid culture media. The composition and concentration of those biological factors can differ based on the growth conditions of the cells and the produced CCM is an undefined composition of matter. Akin to a serum supplement used in the culture of mammalian cells the undefined CCM is used as a supplement to enhance the survival, growth and function of a target cell population. CCM have been produced from a wide range of cells or cell lines (fibroblasts, immune cells, endocrine cells, glia, etc) and used to supplement culture media for the growth of target cell populations. Historically these undefined complex CCM supplements have been used to culture cells without knowledge of the specific CCM bioactivity. The inability to define a bioactivity for a CCM has limited commercial production and availability and consequently most CCM is produced in-house by laboratories. Herein we describe a cell whose survival and growth in culture is dependent on a CCM can be used as a cell-based bioassay to validate and define a specific bioactivity for a CCM and thereby provide a mean of optimizing the production and standardization of CCM supplement for cultured cells. While recognizing the variability present in CCM, exemplary biological factors or products include but are not limited to Cytokines, growth factors, hormones.

Macrophage condition medium (MCM) has been shown to support hybridoma cell survival and growth after cellular fusion with splenocytes from immunized mice (8, 10, 17). The duration of MCM supplementation of hybridoma cells varies during the cloning process as cell stabilization and the production of essential growth factors by the expanding cell population is sufficient for MCM independence. Thus MCM plays a critical role in initial hybridoma stabilization and subsequent growth from a single cell into a clonal cell line producing a monoclonal antibody. Yet MCM is an undefined supplement and differences in production can result in unpredictable bioactivity. Poor quality MCM will likely hinder hybridoma cell growth and impede the selection of desired antibody producing cell lines. In this report we characterize the RMH359 mouse hybridoma cell line and show that its survival and growth in culture is MCM dose-dependent. We use the RMH359 cell line to determine optimal macrophage growth conditions for the production of MCM in support of hybridoma cell cultures and define a RMH359 bioassay to quantify MCM bioactivity for supplement standardization.

Maximizing hybridoma cell survival is essential to ensure selection of antibody producing cells against target antigen. However, MCM is an undefined supplement and thus its use often results in unpredictable hybridoma growth and survival. Poor quality MCM will likely hinder hybridoma cell growth and impede the selection of desired antibody producing cells lines. The standardization of MCM production and validation of its bioactivity prior to culture supplementation would benefit hybridoma cell culture technology. In this report we characterize a clonal mouse hybridoma cell line (RMH359) and show that its survival and growth is MCM dose-dependent. We use the RMH359 cell line as a bioassay to quantify MCM bioactivity and determine optimal macrophage growth conditions in support of hybridoma survival and expansion.

A method for evaluating MCM hybridoma bioactivity using a MCM-dependent RMH359 hybridoma cell line is disclosed herein comprising the steps of production of CCM or MCM, growth of RMH359 Cells and subsequently performing a cell viability assay on the RMH359 cells.

Production of MCM

Sterile J744A.1 macrophage cells seeded at $1\times10^6$ in a 80 $cm^2$ tissue culture treated flask in 15 mL of RPMI 1640 medium supplemented with 10% PBS and placed in a CO2 incubator. Culture medium should be harvested after 24 h, centrifuged at 3,000×g for 5 min, filter sterilized (PES 0.22 µm), stored at 4 QC, and used within one week or frozen.

Growth of RMH359 Cells

Sterile RMH359 cells seeded at $1\times10^6$ in a 80 $cm^2$ tissue culture treated flask in 15 mL of RPMI 1640 medium supplemented with 10% PBS and 20% MCM and placed in a CO2 incubator.

RMH359 Bioassay

Sterile RMH359 cells should be seeded in a 96-well tissue culture treated flat bottom plates at 5-10K cells/well in 200 uL of media composed of RPMI 1640 supplemented with 10% PBS and dilutions of MCM from 0-50% and placed in a CO2 incubator. A cell viability assay such as MTT can be performed to determine optimal MCM supplementation over time to achieve maximal RMH359 growth. The cell viability of RMH359 cells as determined by absorbance at 570 nm can be used to validate MCM bioactivity and normalize % MCM supplementation between different production batches of MCM and used and normalize the between MCM product to achieve optimized and equivalent performance of MCM supplementation on hybridoma cell growth.

RMH359 Cell Viability and Growth is Dependent on Macrophage Conditioned Medium (MCM)

The optimal conditions for the production of CCM is cell-type dependent. This cell-based bioassay can be used to define the optimal growth conditions of any cell type/s used in the production of CCM.

Macrophage conditioned media (MCM) is used to support the survival and growth of hybridomas following cellular fusion and during cloning. Most hybridoma cells will lose their dependence on MCM after cell cloning and it is often excluded from culture medium during final cell expansion and monoclonal antibody (mAb) production. It is generally accepted that cloned hybridomas will begin to produce necessary autocrine or paracrine growth factors that afford them independence of the MCM supplement when grown at sufficient density.

Macrophages have been known to produce a variety of cytokine growth factors that participate in stabilizing newly formed hybridoma cells and stimulating growth (20). Although hybridoma medium supplements have been formulated with some success they tend to be less effective than MCM and more costly. MCM appears to contain an effective balance of growth factors to promote hybridoma survival and growth. Inducing macrophage cells to increase production of essential factors has resulted in limited gains, the RMH359 cell line provides an effective means to identify the composition and ration of essential hybridoma growth factors.

Given the effectiveness and ease of MCM production it will likely remain the supplement of choice in hybridoma cell culture. Herein is described the RMH359 cell line that functions as a sensitive bioassay to evaluate the bioactivity of MCM used in the establishment of hybridoma cell lines for the production of monoclonal antibodies. The sensitivity of the RMH359 cell bioassay to macrophage derived growth factors provides a new method to optimize and validate MCM production. Furthermore, the RMH359 bioassay provides a metric of MCM bioactivity that allows for batch production normalization and certification as hybridoma culture supplement.

The RMH359 hybridoma was generated through the fusion of splenocytes of a Swiss Webster mouse with Balb/c P3X myeloma cell line. The RMH359 cells are resistant to HAT and growth required PBS and MCM supplementation of culture medium. The RMH3599 cell line was cloned by limiting dilution and produces an indiscriminate monoclonal antibody composed of IgG1 heavy chain and kappa light chain. After clonal establishment and expansion the RMH359 cell line remained dependent on MCM for survival and growth. RMH359 cells failed to generate ascites following intraperotineal inoculation of pristine primed Balb/c mice.

The impact of MCM withdrawal on RMH359 growth was evident by phase contrast microscopy with an initial quiescent period observed after 8 h followed by increasing absorption of trypan blue in non-viable cells after 24 h. This observation indicated that RMH359 cells could be used to evaluate the bioactivity and potency of MCM. Using MTT cell viability assay we showed that growth of RMH359 cell were MCM dose-dependent ($r^2=>0.9$) with maximal stimulation achieved at 50% MCM. Importantly, we show that increasing the density of macrophage cells from $1\times10^6$ to $6\times10^6$ in MCM production was ineffective in increasing MCM potency. Moreover, increased macrophage culture time, from 24 h to 72 h, results in decreased MCM potency. Optimal MCM production was achieved by seeding $1\times10^6$ J774A.1 macrophage in a 80 $cm^2$ flask and harvesting MCM after 24 h and using as a 25-50% supplement in hybridoma culture medium.

There is an inverse relationship between macrophage cell density and bioactivity with the potency resulting from an accumulation of growth stimulators and those that induced cell apoptosis.

RMH3S9 Bioassay for Standardization of MCM Production

Figure 5A:
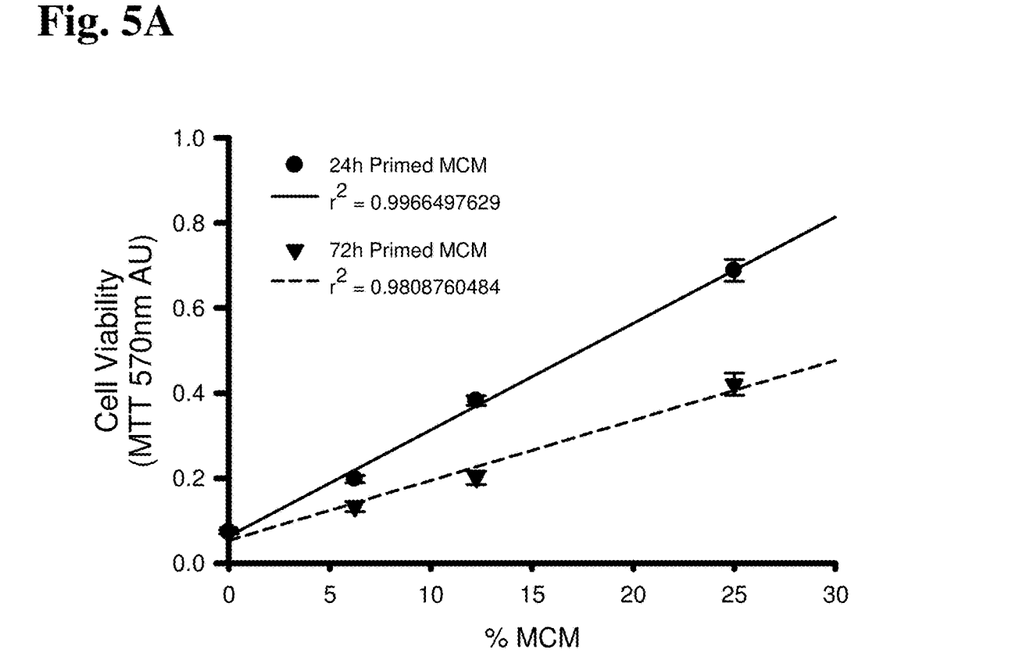
FIGS. 5A and 5B are a compilation of graphs showing the RMH359 cell bioassay for the standardization of MCM bioactivity.

Growth of RMH359 hybridoma cell line is MCM dose-dependent. Data measuring RMH359 hybridoma cell viability with increasing MCM supplementation (0-25%) was used to generate standard curves using linear regression analysis (FIG. 5A). Both 24 h and 72 h macrophage primed MCM stimulate a dose-dependent increase in hybridoma cell viability with linear $r^2$ values >0.98. However, at any given dilution, 24 h primed MCM has a higher efficacy in promoting hybridoma cell viability then an equivalent dose of 72 h primed MCM. Differences in the slope of each line are consistent with the 2-fold higher potency of 24 h primed MCM as compared to 72 h primed MCM (respective b[1] value of 0.025 and 0.014).

Figure 5B:
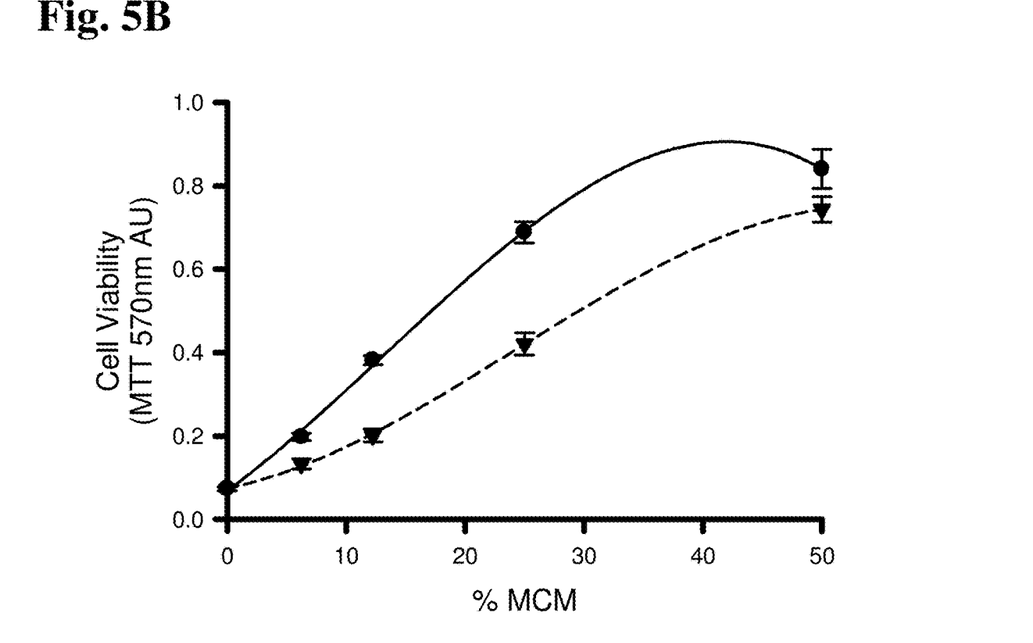

Analysis of RMH359 cell viability data that includes 50% MCM supplementation is best described by a third order regression line (FIG. 5B). The correlation coefficient for 24 h primed MCM for the entire data set is $r^2$=0.9990 when described by third order regression line compared to $r^2$=0.9046 as a first order equation. Although there is a significant difference between 50% and 25% MCM supplementation (P=0.01) on RMH359 cell viability, the change in dose-response between these two dilutions is limited to an increase of ~20%. These data suggest hybridoma culture media supplemented with ~40% 24 h primed MCM will maximize hybridoma cell viability. The dose-response doubling is maintained from 0-50% 72 h primed MCM with nearly identical correlation coefficient described by third order ($r^2$=0.9998) or first order ($r^2$=0.9954) regression lines. There is no statistical difference on cell viability between 50% MCM supplementation from 24 h or 72 h primed MCM suggesting a diminished bioactivity at MCM dilutions >40%.

This standard curve served as a bioassay for standardizing MCM batches as shown by FIG. 5B. Only the linear portion of the standard curve, RMH359 hybridoma supplemented with 0%-25% 24 hr primed MCM, was used for simplicity. To demonstrate the function of this bioassay in determining the bioactivity of unknown MCM, a titration curve was generated for MCM collected under sub-optimal conditions (collected after 72 hr of macrophage growth). Based on the 72 hr primed MCM regression line, the use of 6.25% MCM generated a growth value of 0.13 for RMH359 cells by MTT assay. This would be equivalent to 3% MCM on the standard curve (24 hr primed MCM). Based on the standard curve, 18% MCM would generate a cell viability value of 0.52 (6× of MCM was required to generate this value). For 72 hr primed MCM, 6× of 6.25% MCM would be 37.5%. Based on the 72 hr regression line, this would give a value of 0.57, a relatively similar value to that generated based on the standard curve. This result suggested that for any unknown MCM batch, its bioactivity could be empirically determined by supplementing a given concentration to RMH359 cells to obtain a growth value by MTT. By comparing this value to the standard curve, the amount of unknown MCM required to achieve optimal hybridoma viability could be calculated.

To understand the mechanism of RMH359 cell death we evaluated cell viability in relation to apoptosis in the presence or absence of MCM over time. Here we measured cell viability by cleavage of cell-permeant peptide substrate glyclphenylalanyl-aminofluorcoumarin (GP-AFC) into aminofluorcoumarin (AFC) to generate a fluorescent signal (RFU 485ex/505em). Cells plated in medium containing 50% MCM results in a time-dependent increase in viable cells with a doubling time of ~24 h. RMH359 cells plated without MCM remain viable for 24 h, but do not divide. By 48 h, there is a significant decrease in viable RMH359 cells that remains unchanged after 72 h consistent with cell death. To determine the mechanism of RMH359 cell death we evaluated the activity of the caspase 3/7 apoptosis biomarkers (18) following MCM withdrawal. After 24 h there was a significant rise (>2-fold) in caspase 3/7 activity that fell below basal levels after 48 h. Together with cell viability data this suggests the following MCM withdrawal there is a 24 h period of senescence followed by caspase mediated apoptosis and cell death. Interestingly, MCM stimulates RMH359 cells division with a progressive rise in viable cells (expanding population) but also caspase mediated apoptosis. Despite ongoing apoptosis the rate of cell division exceeds that of cell death and there is an increase in cell number. Therefore in the absence of MCM, RMH359 cell division first stops and then is followed by caspase mediated apoptosis. Conversely, MCM provides the necessary factors to drive the rate of RMH359 cell division to outpace that of apoptosis.

There is a linear relationship between RMH359 cell growth and MCM concentration. Our data analyzed as a first order linear regression we find the goodness-of-fit (r2) for 24 h and 72 h primed MCM are equivalent (>0.99), however the slope of the lines differ with regression coefficients being 0.025 with 0.014 respectively (FIG. 5B).

This suggests that the rate at which macrophage cells produce growth promoting hybridoma cell factors is influence by their time in culture (24 h vs 72 h) which in term reflects their cell density. Indeed, J744 cells have a doubling time of ~24 h and growth is not contact inhibited after 72 h (data not shown). Our interpretation is that after prolonged macrophage culture (72 h) there is a shift in the ratio of secreted stimulatory growth factors toward those that induce apoptosis resulting in less viable hybridoma cultures.

Increased MCM production time is inversely related to RMH359 cell viability. Thus after 72 h there is a decrease in the efficacy MCM on hybridoma viability that requires increased MCM concentration to achieve cell viability levels equivalent to MCM produced after only 24 h. Yet, the linear relationship between increased concentration of MCM and RMH359 cell viability is limited, with a decreasing rate of return with MCM concentrations of 50%. Increasing the concentration of MCM above 50% results in decreased bioactivity (data not shown) suggesting maximal dilution of complete hybridoma culture medium is at a 50% MCM threshold. Therefore, optimized MCM production conditions are essential to achieve maximal growth as one cannot increase the concentration MCM indefinitely to offset MCM production variability.

The MCM dose-dependent growth of RMH359 cells is perhaps better described by third order polynominal regression line to create a standard curve for interpolation. Inclusion of the 50% MCM dilution from 24 h primed macrophage on RMH359 cell viability would yield a r2 value of 0.999 versus 0.904 as a first order regression line. More importantly, the respective slopes would be 0.021 versus 0.016.

Indeed, growth promoting there is a linear relationship between macrophage cell density and production time of MCM as well as the concentration of MCM supplementation on RMH359 cell viability.

Thus our interpretation that there is a shift in the ratio of macrophage produced growth promoting factors to those that favor apoptosis, a consequence of increased macrophage cell density as a function of initial seeding or time in culture. Additionally, as the RMH359 hybridoma cells expand they likely produce paracrine factors that also modulate cell growth versus apoptosis. Indeed, most hybridomas will lose their dependence on MCM for continued growth the growth promoting function usurped by the hybridoma cells themselves. The RMH359 cells favor apoptosis over cell division, but the addition of MCM will promote cell division that outpaces apoptosis.

The rate to maximal MCM concentration in support of RMH359 cell viability is dependent on the MCM production time. Thus as the addition of 50% MCM supplementation to hybridoma medium represents a dilution threshold, the most effective production of MCM is with reduced macrophage density and culture time. The generation of these standard curves from the RMH359 bioassay can then used to evaluate the differences in the efficacy of MCM batch production and used to normalize MCM supplementation.

Figure 1:
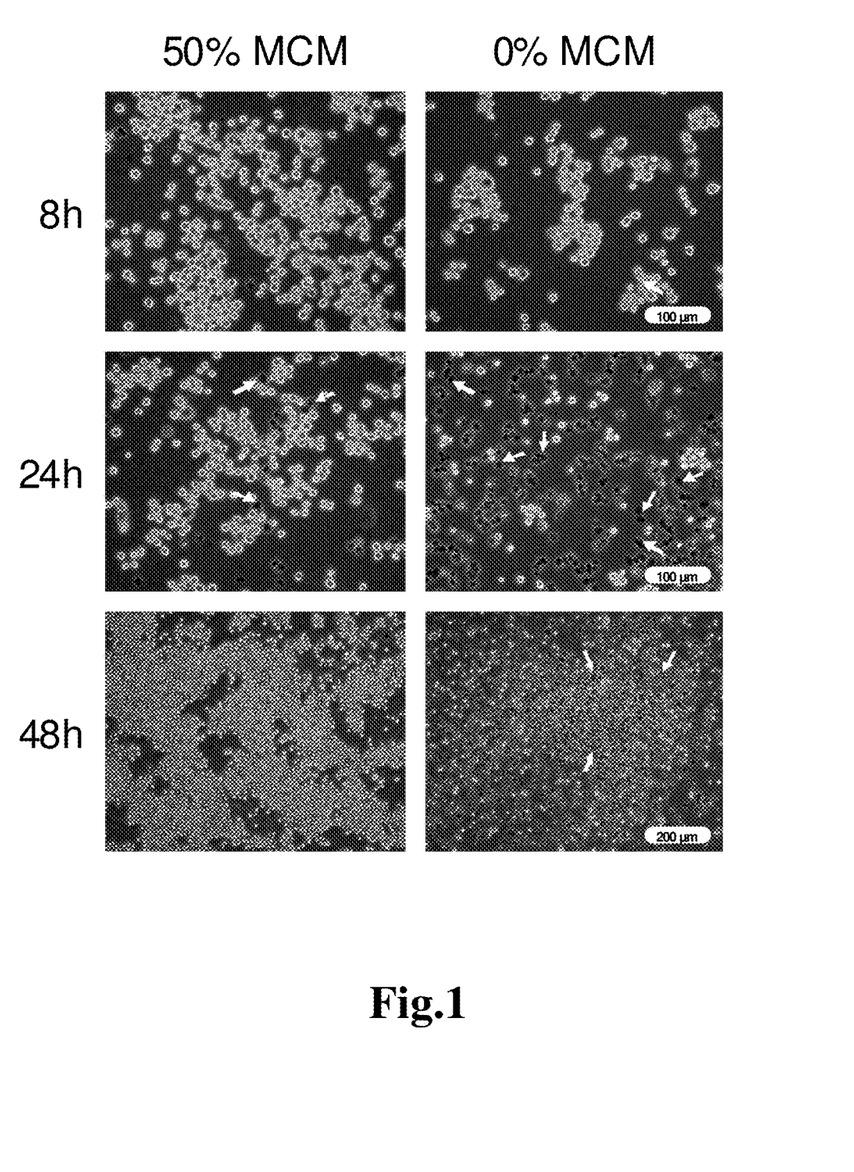
FIG. 1 is a photo panel demonstrating that the viability of RMH359 hybridoma cell line depends on supplementation with macrophage conditioned media (MCM). Phase contrast photomicrographs of RMH359 hybridoma cell line grown in culture medium supplemented with 50% or 0% MCM. Active cultures were treated with 0.2% Trypan blue after 8, 24, and 48 hours (h). Arrows indicate non-viable Trypan blue stained cells.

An equivalent number of RMH359 cells were seeded in medium containing 50% MCM or no MCM and cells evaluated in the presence of Trypan blue after 8, 24, and 48 h by phase contrast microscopy (FIG. 1). Healthy RMH359 hybridoma cells are round, ~25 μm in diameter, and grow as loosely-attached clusters that form plaque-like colonies 48 h after seeding (FIG. 1; left panels). We used a dye exclusion method to evaluate live and dead cells in culture by microscopy. Trypan blue is a vital stain that does not cross the intact membranes of living cells, but is selectively absorbed by dead cells which color blue. At 8 h, the majority of cells cultured in either 50% or 0% MCM were viable with very few dead Trypan blue stained cells observed (FIG. 1A-B). However, there did appear to be fewer total live cells after 8 h growth in MCM-free medium compared to those grown in 50% MCM. By 24 h we observed a dramatic difference in the number of viable RMH359 cells; with most cells grown in 50% MCM being viable (FIG. 1C) as compared to the majority of cells grown in MCM-free medium having absorbed the Trypan blue dye (FIG. 1D). After 48 h of culture, cells grown in 50% MCM had proliferated and formed large attached colonies with few Trypan blue positive cells observed (FIG. 1E). In contrast, the majority of RMH359 cultured in MCM-free medium after 48 h were Trypan blue positive and non-viable (FIG. 1F).

RMH359 Bioassay for Standardization of MCM Production

Complete medium for RMH359 cells is defined as RPMI 1640 medium, 20% PBS, 40% MCM, 1× HT, and 1× penicillin/streptomycin. Alternative rich media such as Iscove's can replace RPMI 1640 and the addition of HT or pen/strep is not required. Supplementation with PBS can be adopted between 5-20%. MCM is essential component for RMH359 cells survival and can be used at 5-50% with increasing concentrations resulting in improved survival and cell growth.

Using RMH359 cell viability as metric we evaluated the stability of the hybridoma cell culture supplements by comparing those prepared from fresh stock stored at 4 C to those pre-incubated for 7 or 14 d at 37 C in 5% CO2. Complete medium composed of all supplements showed a progressive decline in bioactivity of ~20% every 7 d at 37 C 5% CO2. Fetal bovine serum was unaffected by pre-incubation of stock material at 37 C with equivalent bioactivity to material stored at 4 C when used at 10% in complete medium. The bioactivity of MCM was unchanged after 7 d pre-incubation at 37 C, but after 14 d there was ~30% decline in bioactivity. These data shows that the bioactivity of filter sterilized MCM remains stable at 4 C and is suitable for short-term storage during active cell culture. Freezing MCM does not adversely affect bioactivity (data not shown) and is therefore suggested for longer-term storage. Importantly, the progressive decline in the bioactivity of complete medium at 37 C/5% CO2 (~20% every 7 d), which is independent of cells, suggests replacement in active culture every 10 d to maximize hybridoma survival and growth.

Data measuring RMH359 hybridoma cell viability with increasing MCM supplementation (0-25%) was used to generate standard curves using linear regression analysis (FIG. 5A). Both 24 h and 72 h macrophage primed MCM stimulate a dose-dependent increase in hybridoma cell viability with linear $r^2$ values >0.98. However, at any given dilution, 24 h primed MCM has a higher efficacy in promoting hybridoma cell viability then an equivalent dose of 72 h primed MCM. Differences in the slope of each line are consistent with the 2-fold higher potency of 24 h primed MCM as compared to 72 h primed MCM (respective b[1] value of 0.025 and 0.014).

Analysis of RMH359 cell viability data that includes 50% MCM supplementation is best described by a third order regression line (FIG. 5B). The correlation coefficient for 24 h primed MCM for the entire data set is $r^2=0.9990$ when described by third order regression line compared to $r^2=0.9046$ as a first order equation. Although there is a significant difference between 50% and 25% MCM supplementation (P=0.01) on RMH359 cell viability, the change in dose-response between these two dilutions is limited to an increase of ~20%. These data suggest hybridoma culture media supplemented with ~40% 24 h primed MCM will maximize hybridoma cell viability. The dose-response doubling is maintained from 0-50% 72 h primed MCM with nearly identical correlation coefficient described by third order ($r^2=0.9998$) or first order ($r^2=0.9954$) regression lines. There is no statistical difference on cell viability between 50% MCM supplementation from 24 h or 72 h primed MCM suggesting a diminished bioactivity at MCM dilutions>40%.

This standard curve served as a bioassay for standardizing MCM batches as shown by FIG. 5B. Only the linear portion of the standard curve, RMH359 hybridoma supplemented with 0%-25% 24 hr primed MCM, was used for simplicity. To demonstrate the function of this bioassay in determining the bioactivity of unknown MCM, a titration curve was generated for MCM collected under sub-optimal conditions (collected after 72 hr of macrophage growth). Based on the 72 hr primed MCM regression line, the use of 6.25% MCM generated a growth value of 0.13 for RMH359 cells by MTT assay. This would be equivalent to 3% MCM on the standard curve (24 hr primed MCM). Based on the standard curve, 18% MCM would generate a cell viability value of 0.52 (6× of MCM was required to generate this value). For 72 hr primed MCM, 6× of 6.25% MCM would be 37.5%. Based on the 72 hr regression line, this would give a value of 0.57, a relatively similar value to that generated based on the standard curve. This result suggested that for any unknown MCM batch, its bioactivity could be empirically determined by supplementing a given concentration to RMH359 cells to obtain a growth value by MTT. By comparing this value to the standard curve, the amount of unknown MCM required to achieve optimal hybridoma viability could be calculated.

Macrophage Culture Conditions for Optimized MCM Production in Support of Hybridoma Cells.

Fetal serum as a culture supplement provides a rich source of growth factors that are necessary for the growth of most primary cells and immortal cell lines. Although serum supplementation is sufficient for continued culture of immortal myeloma cell lines, the survival of primary splenocytes is time limited. Importantly, myeloma cells, unlike splenocytes, cannot produce nucleotides by de novo or salvage pathways and culture in HAT (hypoxanthine-aminopterin-thymidine) supplemented medium, which blocks nucleotide synthesis, causes them to die. The cellular fusion of an immortalized myeloma cell with a splenocyte results in a hybrid cell with DNA from both cell types. Thus hybrid cells inherit properties from both parent cells that make them resistant to HAT and immortal. Newly fused hybrid cells are fragile and survival is likely dependent on a transition period in culture resulting in cell stabilization followed by growth and antibody production. Macrophages secrete a wide range of biologically active immune cell mediators and the use of MCM as a culture medium supplement is thought to facilitate the establishment of hybridoma cell lines after cellular fusion. Yet, optimal culture conditions for the production of MCM are poorly defined as survival, selection, and growth of clonally expanded hybridoma cell lines often become independent of MCM. The novel RMH359 hybridoma cell line remains dependent on MCM for survival and their growth is MCM dose-dependent. We have characterized a RMH359 cell bioassay that defines optimal conditions for the production and standardization of MCM as a supplement for use in hybridoma cell culture.

Figure 2A:
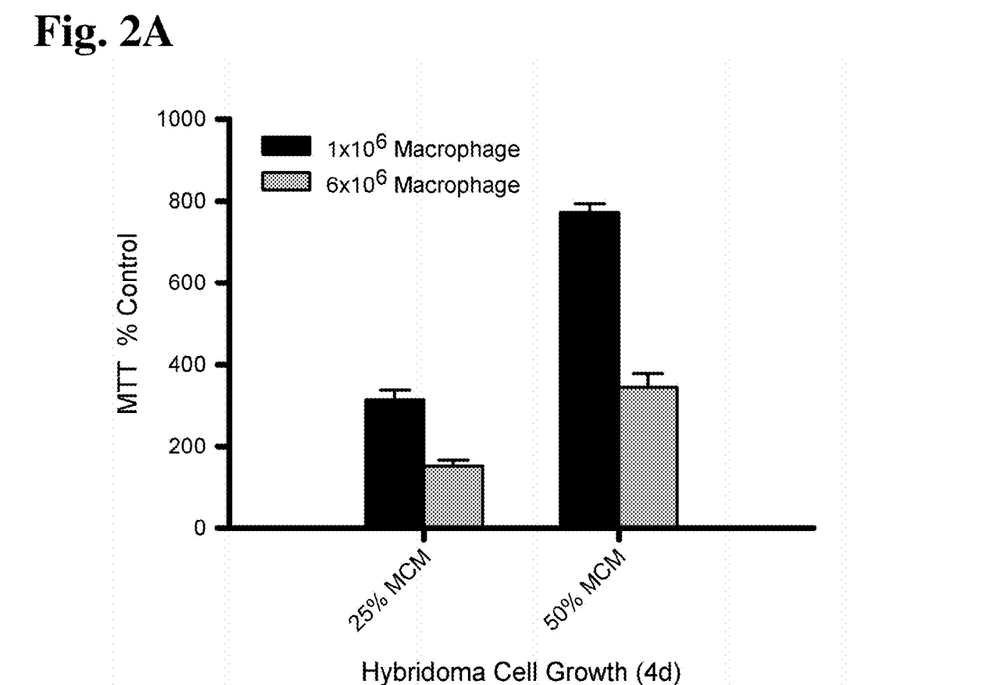
FIGS. 2A and 2B are a compilation of graphs demonstrating that the growth and survival of RMH359 hybridoma cell line is MCM dose-dependent.

The J744A.1 macrophage cell line was used to define optimal MCM production in support of RMH359 hybridomas in culture. First, J744A.1 cells were seeded at two different densities in 80 cm$^2$ flasks (1 or 6×10$^6$ cells) in 15 mL of macrophage growth medium for 24 h to generate 100% MCM. RMH359 cells were plated in 96-well microplates and cultured in hybridoma medium supplemented with 25% or 50% MCM for 4 d and cell viability determined by MTT assay and expressed as % of MCM-free control (FIG. 2A). MCM improved cell viability of RMH359 cells relative to MCM-free control (2-8 fold) and hybridoma growth showed MCM dose-dependence with 25% MCM half as effective as 50% MCM in promoting hybridoma growth. Interestingly, increased density of the initial macrophage seed resulted in MCM that was significantly less effective, at either concentration, in promoting RMH359 cell growth (P<0.05). Suggesting a 1×10$^6$ macrophage cell seed per 80 cm$^2$ is the optimal density of macrophage cells to yield an effective MCM supplement to support hybridoma cell growth. Maximal RMH359 cell growth (8-fold) was achieved using 50% MCM generated from 1×10$^6$ macrophage cells.

Figure 2B:
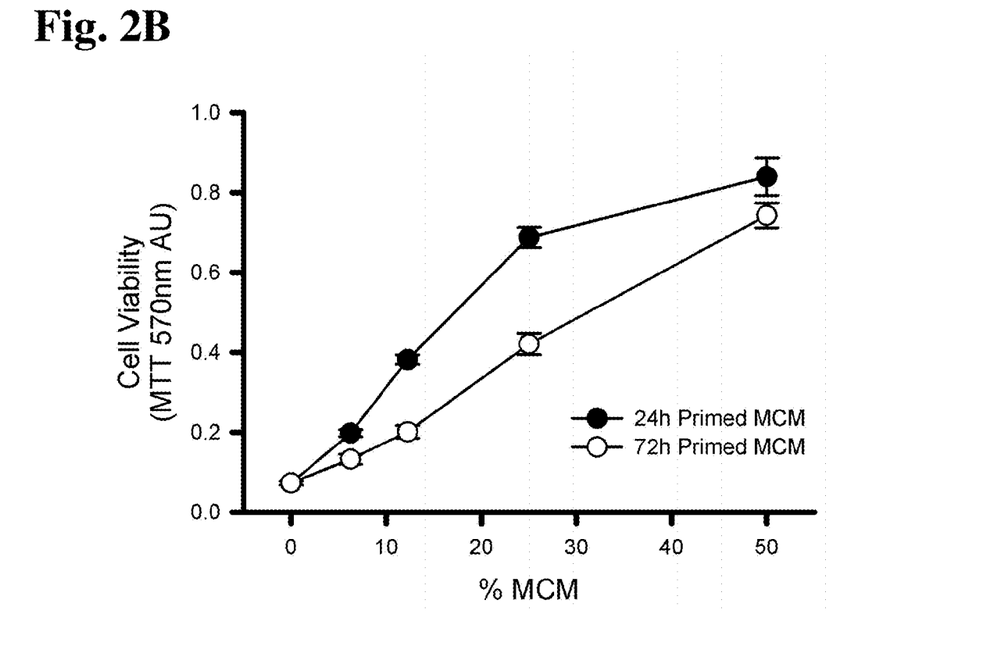

Once we determined the macrophage seeding density and optimal concentration of MCM to achieve maximal hybridoma growth we evaluated the impact of macrophage growth time on production of MCM in support of RMH359 cell growth. Macrophage cells at 1×10$^6$ were cultured for 24 or 72 h and the resulting primed MCM was used to demonstrate the dose-dependent growth of RMH359 on MCM after 4 d by MTT (FIG. 2B). At all dilutions tested, 72 h primed MCM was less effective than 24 h primed MCM in supporting RMH359 cell viability. Indeed, 25% 24 h primed MCM has equivalent bioactivity as 50% 72 h primed MCM. However, at 50% MCM the difference in cell viability between 24 h and 72 h primed MCM decreased, suggesting a 50% dilution is near maximal for effective hybridoma survival and growth supplementation. Indeed, dilutions of MCM above 50% were less effective in supporting RMH359 cell viability (data not shown). The absence of MCM (0%) resulted in non-viable RMH359 cells with MTT absorbance values equivalent to wells with no cells.

Figure 3A:
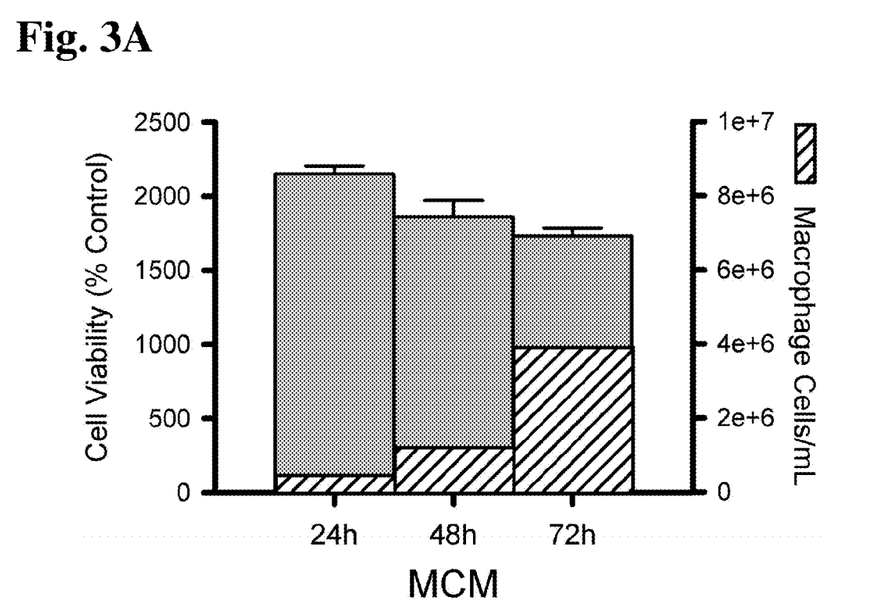
FIGS. 3A and 3B show a compilation of graphs showing optimization of MCM production and stability in growth medium.

RMH359 hybridoma cells supported by 50% MCM collected after 24 h did result in a statistically higher cell viability (P<0.05) than either 48 h or 72 h primed MCM (FIG. 3A). We determined macrophage cell number (cells/mL) at the time of MCM harvest and show a time-dependent increase in macrophage cell number which is inversely associated with MCM bioactivity as defined by RMH359 cell viability. These data suggest that optimal production of MCM in support of hybridoma cell growth is with a sub-confluent macrophage density (1×10$^6$/80 cm$^2$) collected after 24 h and used in hybridoma culture medium at a 50% dilution.

Stability of Hybridoma Growth Medium Containing MCM

Figure 3B:
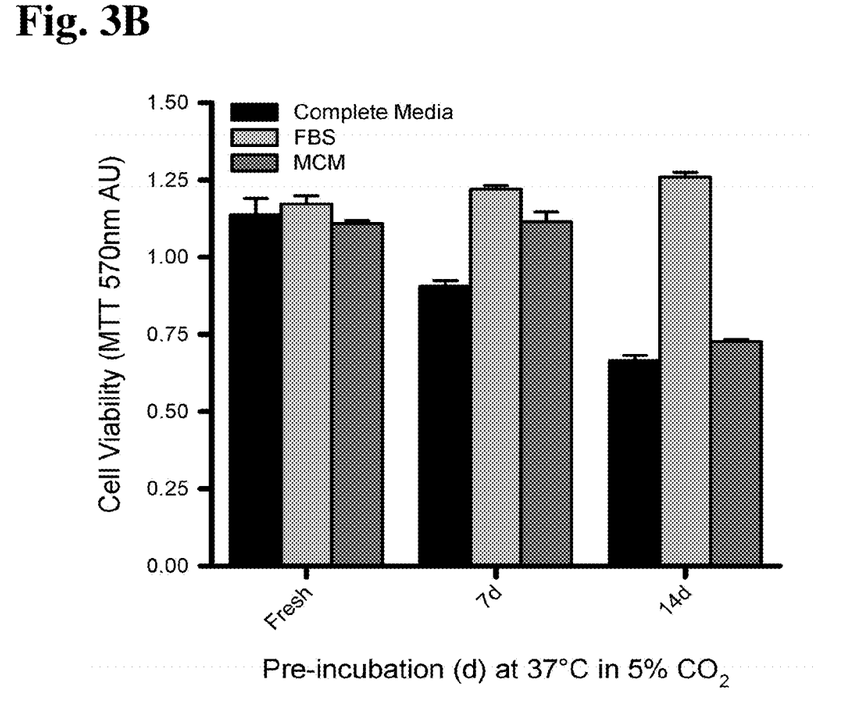

The stability of hybridoma growth medium components at 37° C. in 5% CO2/95% air over time was evaluated using RMH359 cell line (FIG. 3B). Fetal bovine serum (PBS), MCM and the complete growth medium (containing advanced RPMI 1640, 20% PBS, 40% MCM, 1× HT, and penicillin/streptomycin), were used following pre-incubation for 7 and 14 d at 37° C. in 5% CO2. The bioactivity of these pre-incubated components were then compared with freshly prepared medium from stock solutions stored at 4° C. for 4-weeks on RMH359 cell viability after 4 d of growth. The pre-incubation of PBS up to 14 d had no effect on cell viability when used to make complete medium. The stability of MCM was maintained through 7 d pre-incubation, but showed a precipitous decline in bioactivity after 14 d pre-incubation. Pre-incubation of complete medium resulted in a time-dependent decline in bioactivity with −30% reduction every 7 d. The difference in hybridoma support profile between complete medium and MCM was likely a result in depletion of advanced RPMI 1640 components. These data suggest that complete hybridoma media replenishment after −10 d of growth would minimize the loss (−30%) of viable cells as a result of depleted medium components.

The Absence of MCM Results in RMH359 Cell Apoptosis

Figure 4A:
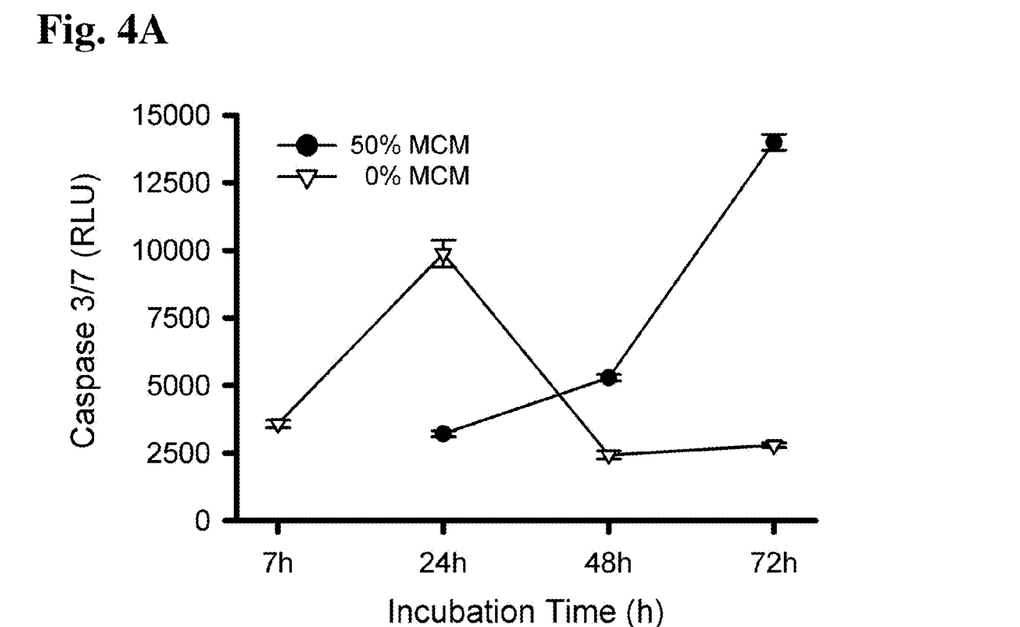
FIGS. 4A and 4B are a compilation of graphs showing MCM withdrawal results in Caspase mediated apoptosis.

In order to establish the mechanism of RMH359 cell death we compared caspase-3 and -7 activities from cells following MCM withdrawal to those grown in culture medium supplemented with 50% MCM (FIG. 4A). The withdrawal of MCM supplement resulted in a significant spike in caspase activity (P<0.05) at 24 h followed by a return to levels equivalent to assay background at 48 and 72 h time points. By comparison, cells grown with 50% MCM supplementation showed elevated caspase activity beginning after 48 h followed by an exponential rise by 72 h.

Figure 4B:
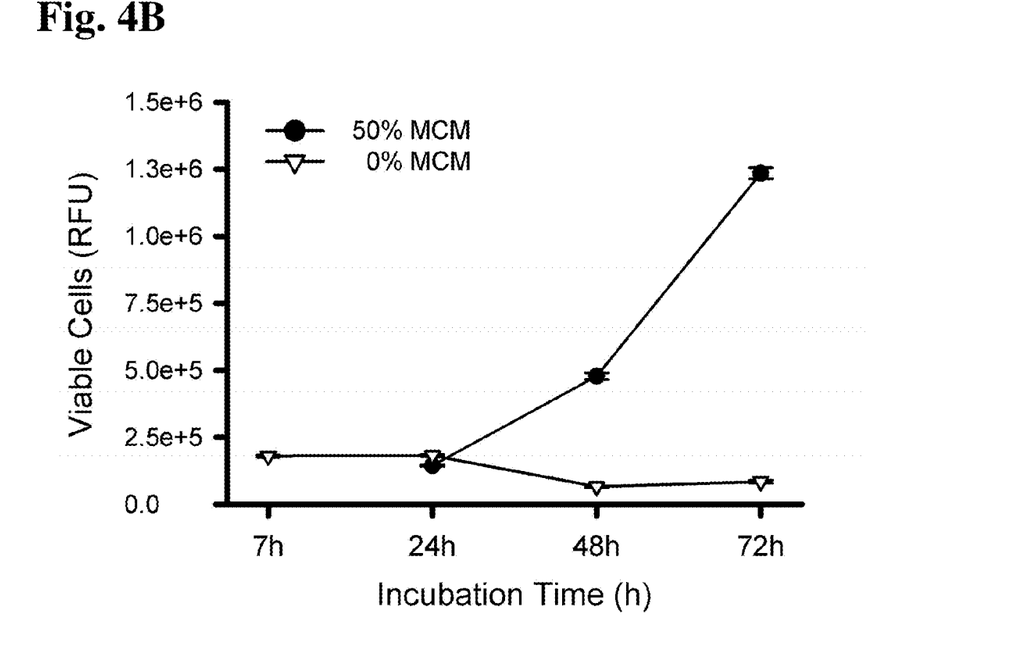

Cell viability as measured by the CytoTox-Glo™ cytotoxicity assay shows no remaining viable RMH359 cells 48 h after the withdrawal of MCM (FIG. 4B). By contrast, hybridoma cells seeded at the same density, but maintained in 50% MCM showed an increase in viable cell number over time. These data show that with MCM supplementation the rate of RMH359 cell division is greater than the rate of apoptosis resulting in increasing cell number. The increase in apoptosis in MCM supplemented cultures may reflect resource consumption of cells as they reach a certain density. This may explain the delayed onset of apoptosis observed in MCM supplemented cultures. MCM likely provides essential factors that promote cell growth resulting in dividing cells that outpace those undergoing apoptosis resulting in ever expanding cell number in culture.

Materials and Methods

Generation of RMH359 Hybridoma Cell Line.

Balb/cJ mouse myeloma P3X63AG8U.1 cells (15) were cultured in advanced RPMI 1640 (Invitrogen, CA; #12633) supplemented with 10% heat-inactivated Fetal Bovine Serum (PBS), 2 mM Glutamax-1 (Invitrogen, CA; #35050), and 100 ug/ml penicillin/streptomycin in flasks with 80 cm$^2$ culture area (NUNC 178905). Myeloma cells were split 24 h prior to fusion with splenocytes from a female Swiss Webster mouse (CFW®; Charles Rivers Laboratory, MA) immunized with hamster brain preparation. Cells were mixed at 1:1 ratio and centrifuged for 10 min at 1,700 rpm. The resulting cell pellet was slowly suspended in 1 mL of 50% polyethylene glycol (Sigma-Aldrich, MO; P7181) followed by 9 mL of advanced RPMI 1640. Hybrid cells were cultured in complete medium composed of advanced RPMI 1640 supplemented with 20% PBS, 40% MCM, 0.1 mM sodium hypoxanthine, 0.4 µM aminopterin, 0.016 mM thymidine, and 100 µg/ml penicillin/streptomycin for 4 d before feeding with the same growth medium without the addition of aminopterin. Hybridoma cells were selected by antibody binding to hamster brain extract using indirect ELISA and cloned 2× by limiting dilution. Of the surviving hybridoma cell clones, one was designated RMH359 which produced a monoclonal antibody with IgG1 heavy and kappa light chains. Culture supernatant containing monoclonal antibody (mAb) produced by the RMH359 showed no specific binding to brain homogenates by either indirect ELISA or Western blot and is characterized as a non-binding mAb. Additionally, RMH359 hybridoma cells failed to produce ascites in pristine-primed Balb/cJ mice (Covance, CO; N=10).

Microscopic Analysis

RMH359 cells were seeded at 40,000 cells/well in 6-well multidish plates (NUNC 140675, 9.6 cm$^2$) in complete medium containing either 50% MCM or 0% MCM. Trypan blue dye exclusion was used to evaluate cell viability by the addition of 0.1 ml of a 0.4% Trypan blue solution per 0.5 ml of cell suspension after 8 h, 24 h and 48 h of cell culture. Phase contrast digital micrographs were taken with Leica DMI 4000B after incubation of cells with Trypan blue for 3 mm.

Macrophage Cell Culture and Preparation of Macrophage Condition Media (MCM)

J744A.1 macrophage cells were seeded at either 1×10$^6$ or 6×10$^6$ cells in culture flasks (NUNC 178905, 80 cm$^2$) with 15 mL of advanced RPMI 1640 medium supplemented with 10% heat-inactivated PBS, 5.5×10$^{-5}$ M beta-mercaptoethanol (Invitrogen, CA; #21985-023), 0.5 µg/ml bovine holo-transferrin (Invitrogen, CA; #11107-018), 2 mM Glutamax-1, and 10 mM HEPES buffer (Sugasawara, 1985 PMID: 3998479). Culture medium was collected after 24-72 h of cell growth as macrophage conditioned media (MCM), centrifuged at 3,000×g for 5 min, filter sterilized (PES 0.22 µm), stored at 4 QC, and used within one week.

MIT Assay

A second measurement of cell viability was performed by MTT assay measuring the reduction of MTT (3-(4,5-dimethylthiazole-2-yl)-2,5-diphenyl tetrazolium bromide, Sigma-Aldrich Corporations, MO; #M2128) by viable cells to formazan (Berridge 2005 PMID:16216776). The MTT assay performed was similar to that originally described by Mosmann (16). 4000 RMH359 cells were plated in 96-well culture plates (NUNC) and grown for 4 days in 200 µl of culture medium. MTT was prepared as a filter sterilized stock solution (5 mg/mL in 10 mM phosphate-buffered saline) and added to culture wells at final concentration of 1 mg/mL and then incubated at 37° C. for 4 h. After the formation of formazan salt, the supernatant was discarded and 100 µl of 0.04 N HCl in isopropanol was added to dissolve the purple formazan precipitate accumulated in cell mitochondria. The plate was then incubated at room temperature in the dark for 2 h and the optical density (OD) was measured at a test wavelength of 570 nm and a reference wavelength of 660 nm on SpectraMax M5 (Molecular Devices, CA). The OD measurement reported represents the total amount of formazan detected and serves as an indirect measure of viable cell number. Data represents 16 replicates per data point and is expressed as mean absorbance units (AU) at 570 nm±SEM.

Caspase-Glo 317 Assay

To measure the rate of apoptosis in the absence of MCM, apoptotic markers caspase-3 and -7 (Lakhani 2006 PMID: 16469926) activities were measured using the Caspase-Glo 3/7 assay (Promega, WI; #08091). RMH359 cells were plated at two different densities (400 cells and 4000 cells) in 96-well plates and allowed to attach for 24 hours in complete medium with 50% MCM before switching to 100 µl of medium containing 0% or 50% MCM and grown for and additional 7, 24, 48, and 72 h. A 1:2 dilution of Caspase 3/7 luminogenic substrate containing the caspase target sequence (DEVD) was added to each well and incubated for 1 h. Cleavage of the DEVD sequence by caspase-3 and -7 results in luminescent signal that is proportional to their cellular activities. Luminescence was measured on a Victor X3 plate reader for 0.2 sec (PerkinElmer, MA) and data represents 12 replicates per time point and is expressed as mean relative light units (RLU)±SEM.

CytoTox-Glo™ Cytotoxicity Assay

Cell viability in the absence of MCM was measured by a CytoTox-Glo™ Cytotoxicity Assay (Promega, WI; #TB359). This assay measures cleavage of an AAF-Glo™ substrate by proteases that are released from dead cells. Cells were plated the same way as described for Caspase-Glo 3/7 assay. After switching to medium containing 0% or 50% MCM, 50 µl of AAF-Glo™ reagent was added directly to cells growing in 100 µl culture medium. The cells were then incubated with the glyclphenylalanyl-aminofluorcoumarin substrate (GP-AFC) for 15 minutes allowing the proteases from dead cells to cleave the substrate into aminofluorcoumarin (AFC) and generate a fluorescent signal (485/505 nm). The luminescent signal was recorded on a Victor X3 as described then followed by the addition of the detergent digitonin to lyse remaining viable cells and a second luminescent reading recorded. The difference between the two luminescent signals is a measure of viable cells per well. The data represents 12 replicates per time point and is expressed as mean relative fluorescent units (RFU)±SEM.

Statistical Analysis

Kruskal-Wallis one way analysis of variance on ranks was used for comparison of all treatment groups within an assay followed by Mann-Whitney U Rank Sum test of individual pairs. A value P<0.001 was considered statistically significant. Curve fitting was performed by Sigma Stat Software (Systat, CA) and the RMH359 titration standard curve was fitted by a third-order polynomial regression line.

What is claimed:

1. A composition comprising a conditioned media dependent hybridoma cell line deposited under accession number ATCC PTA-122116 and a cell conditioned media.

2. A bioassay method for testing a macrophage conditioned media to determine whether said macrophage conditioned media promotes growth and sustains cell viability of cells of hybridoma cell line deposited under accession number ATCC PTA-122116, the method comprising:
   (1) producing a macrophage conditioned media;
   (2) culturing cells of hybridoma cell line deposited under accession number ATCC PTA-122116;
   (3) seeding the cultured cells of the hybridoma cell line of (2) with the macrophage conditioned media of (1); and
   (4) measuring cell growth and survival of the cultured cells seeded in (3) to determine cell viability of said cultured cells, thereby testing the macrophage conditioned media.

* * * * *